: US 7,462,169 B2

(12) United States Patent
Follman et al.

(10) Patent No.: US 7,462,169 B2
(45) Date of Patent: *Dec. 9, 2008

(54) SAFETY SHIELD SYSTEM FOR AN INJECTION PEN NEEDLE

(75) Inventors: Mark A. Follman, New Jersey, NJ (US); David R. Stonehouse, Cambridge (GB); Michael J. Newman, Hunsdon Ware Herts (GB)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/626,209

(22) Filed: Jan. 23, 2007

(65) Prior Publication Data

US 2008/0177238 A1  Jul. 24, 2008

(51) Int. Cl.
*A61M 5/32* (2006.01)
(52) U.S. Cl. .................... 604/198; 604/192
(58) Field of Classification Search ............. 604/198, 604/192, 110, 117, 263, 181, 187, 197
See application file for complete search history.

(56) References Cited

U.S. PATENT DOCUMENTS

| | | | | |
|---|---|---|---|---|
| 4,921,491 A * | 5/1990 | Champ | | 604/199 |
| 5,030,209 A | 7/1991 | Wanderer et al. | | |
| 5,290,254 A | 3/1994 | Vailliancourt | | 604/192 |
| 5,336,200 A | 8/1994 | Streck et al. | | 604/198 |
| 5,403,286 A | 4/1995 | Lockwood, Jr. et al. | | 604/110 |
| 5,423,758 A | 6/1995 | Shaw | | 604/110 |
| 5,545,145 A | 8/1996 | Clinton et al. | | 604/192 |
| 5,658,259 A | 8/1997 | Pearson et al. | | |
| 5,681,291 A * | 10/1997 | Galli | | 604/192 |
| 5,725,508 A | 3/1998 | Chanoch et al. | | 604/207 |
| 5,827,232 A | 10/1998 | Chanoch et al. | | 604/208 |
| 5,893,845 A | 4/1999 | Newby et al. | | |
| 5,928,205 A | 7/1999 | Marshall | | 604/263 |
| 5,941,857 A | 8/1999 | Nguyen et al. | | 604/263 |
| 5,964,739 A * | 10/1999 | Champ | | 604/263 |
| 6,379,337 B1 | 4/2002 | Mohammad | | 604/195 |
| 6,547,764 B2 | 4/2003 | Larsen et al. | | 604/192 |
| 6,595,931 B2 | 7/2003 | Ranford | | |
| 6,986,760 B2 * | 1/2006 | Giambattista et al. | | 604/198 |
| 7,104,969 B2 | 9/2006 | Du Plessis | | 604/110 |
| 2004/0193110 A1 * | 9/2004 | Giambattista et al. | | 604/110 |
| 2005/0038392 A1 | 2/2005 | DeSalvo | | 604/198 |
| 2005/0171485 A1 | 8/2005 | Larsen et al. | | 604/198 |
| 2005/0288607 A1 | 12/2005 | Konrad | | 600/576 |
| 2006/0189933 A1 | 8/2006 | Alheidt et al. | | |

FOREIGN PATENT DOCUMENTS

WO   2004/030539   4/2004

* cited by examiner

*Primary Examiner*—Kevin C Sirmons
*Assistant Examiner*—Shefali D Patel
(74) *Attorney, Agent, or Firm*—Alan W. Fiedler; Fitzpatrick, Cella, Harper & Scinto LLP

(57) ABSTRACT

A safety shield system for a pen needle according to the invention has a first passive safety shield for the injection end of a needle, covering the needle before and after use, and a second passive safety shield for the non-injection end of the needle, covering the non-injection end of the needle before and after use, and locking in the covering position when the pen injector is removed.

8 Claims, 4 Drawing Sheets

SAFETY SHIELD SYSTEM FOR AN INJECTION PEN NEEDLE

BACKGROUND OF THE INVENTION

1. Field of the Invention

The invention is directed to a passive safety shield system associated with an injection pen needle.

2. Description of the Related Art

Accidental needlestick injuries from contaminated needles expose healthcare workers to the risk of infection from blood-borne pathogens, including the viruses that cause hepatitis B and C, and HIV. According to the Centers for Disease Control and Prevention, healthcare workers in the United States experience an estimated 600,000 exposures to blood each year, with RNs being subject to an overwhelming majority of these incidents.

While the injection device of choice in the U.S. remains the syringe, the demand for pen needles is growing rapidly. The use of self-injection injection pen devices is increasing due to the relative convenience, portability, and ease of use of these devices as compared to single use syringes. Pen needles are also becoming more commonplace in the hospital/clinical setting, as certain drugs, such as human growth hormone and osteoporosis medications, are available only in pen needle format.

Healthcare workers have sustained needlestick injuries while removing and disposing of needle hubs from pen needle devices after administering an injection to patients. The needles are typically removed after each injection to minimize contamination of the medication in the cartridge and to prevent needle re-use. Removal of the needle generally requires the re-shielding of the needle using the outer protective shield in which it was supplied and it is especially during the re-shielding step where injuries can occur. Needlestick injuries also occur during the removal of pen needles that have not been re-shielded.

U.S. Pat. No. 6,986,760 B2, assigned to the assignee of the present application, the disclosure of which is herein incorporated by reference in its entirety, teaches a pen needle and safety shield system wherein a safety shield, which normally encloses the needle cannula prior to use, permits retraction of the safety shield during injection and automatically extends and locks the shield in the extended enclosed position following use. The pen needle also prevents retraction of the shield during assembly of the shield and needle cannula and hub assembly on the pen injector.

U.S. Pat. No. 6,855,129 B2 discloses a safety needle assembly having a cylindrical housing with a needle mounted thereon for mounting onto a medical injection device. A shield is telescopically movable relative to the housing for movement between a distal position in which the shield covers the end of the needle, and a proximal position in which the needle is exposed. A spring located inside the housing urges the shield in the distal direction. A locking element on the device is provided inside the housing with outwardly pointing locking protrusions. The locking element is a separate part provided between the spring and the shield and it is longitudinally moved simultaneously with the shield relative to the housing during use, so that the protrusions on the locking element are guided from a first position where the shield is in the distal position, to a second position where the shield is in the proximal position, to a third position where the locking protrusions are blocked by a blocking surface provided on the inside surface of the housing, so that further movement of the shield is irreversibly immobilized.

However, the prior art does not disclose an injection pen needle having a non-injection end passive safety shield. The invention disclosed herein, which may be incorporated into prior art safety shielded pen needles, represents an advance in the art, at least in that novel means are provided to guard against accidental needlestick from the non-injection end of a needle in an injection pen needle.

SUMMARY OF THE INVENTION

A safety shield system for an injection pen needle according to the invention comprises shields for both the injection end and the non-injection end of the needle. The needle is mounted in a hub having recesses on opposite ends, each recess surrounding a respective end of the needle, and a hub middle wall separating the ends. In this way, the injection end of the needle extends into one recess and the non-injection end of the needle extends into the other recess.

A first shield, which has an aperture in an end wall thereof for passage of the needle, moves over the outside of the first recess on the hub, coaxially with the hub, from a retracted position, in which the needle is exposed, to a full travel position in which the shield covers the end of the needle. An elastic member housed between the end wall of the shield and the hub middle wall biases the shield toward the full travel position.

In a preferred embodiment, the elastic member is a clip, which fits against the middle wall of the hub and the needle mounting. The clip has a tab, which in a locked position, engages a slot in a radial wall of the hub and the shield to hold the shield in a position covering the needle. The tab may act as an indicator or be provided with an indicator, which can be viewed from the exterior of the device. A "tab" in this context simply means a portion of the clip that is designed to be inserted into another object, by way of a receiving slot, for example. A "slot" may be an aperture or through-slot, and in certain embodiments may simply be a recess.

The system also includes a second shield, situated in the recess on the opposite, non-injection end, of the hub. The second shield has an aperture to permit passage of the non-injection end of the needle into the pen injector. The second shield travels inside the second recess, on the non-injection end of the hub. A second elastic member pressed against the non-injection side of the hub middle wall holds the non-injection end shield toward the non-injection end of the hub in the full travel position. Thus, the non-injection end shield travels from a compressed position, in which the needle is inserted into the septum of a pen injector in the non-injection end of the hub, to a full travel position in which the shield covers the non-injection end of the needle when the pen injector is removed, held in place by the elastic member.

In preferred embodiments a further biasing element, such as a spring or other elastic member, or a gas-filled piston, or the like, is located between the second shield and the hub, is compressed when the pen injector is installed, and urges the second shield to cover the non-injection end of the needle when the pen injector is removed.

DETAILED DESCRIPTION OF THE PREFERRED EMBODIMENTS

The safety shield system according to the invention is "passive" because the shielding of the non-injection end of the needle is automatic upon removing the pen injector.

As used herein, the terms "injection end" and "non-injection end" refer to directions on the device, regardless of whether the particular element is involved in the injection. Thus (for example only) the hub and the shields have an injection end and a non-injection end. The injection end is toward the end of the device that is normally pressed against a patient's body to administer an injection, and the non-injection end is toward the opposite end of the device.

A pen needle is generally longer than it is wide. Movement on the longitudinal axis is referred to herein as "axial" movement. The perpendicular direction is the "radial" direction, and the direction traveled when an element is twisted around the longitudinal axis is the "circumferential" direction.

The present invention uses a shield for the non-injection end (also called the "non-patient" end) of a needle, and is advantageously incorporated into a device having a shield at the injection end, such as the Autoshield™ device. As the operation of the injection end shield has thus been previously disclosed, the present invention is described first in connection with the non-patient end shield.

Figure 1:
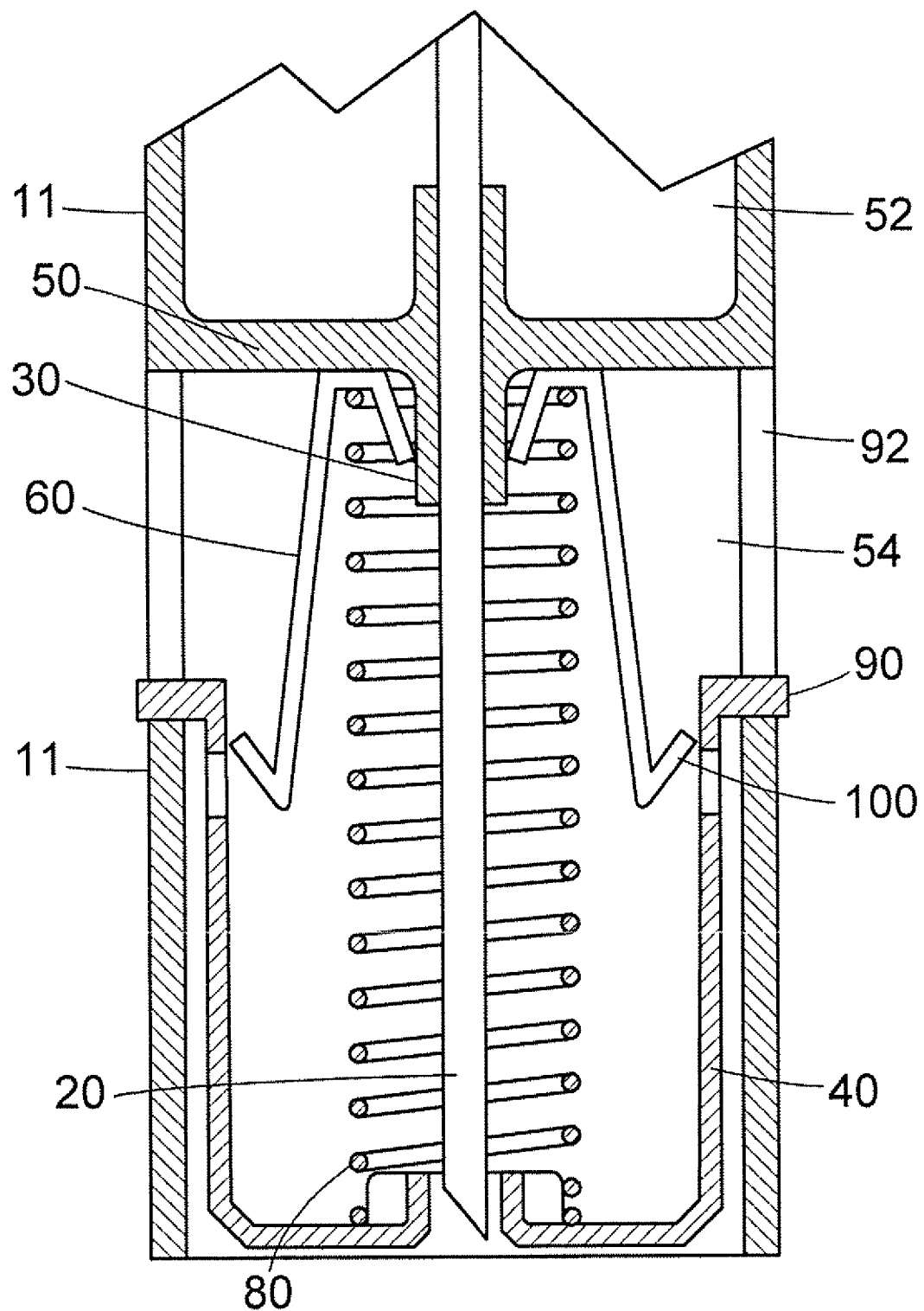
FIG. 1 is a detail of the system according to the invention showing the non-injection end shield covering the non-injection end of the needle, but unlocked, prior to inserting the pen injector.

FIG. 1 is a cross-sectional view through the non-injection end of a safety pen needle according to the invention. FIG. 1 shows the safety pen needle in the unlocked position, i.e., the state when the device is initially assembled and shipped in a sterile outer packaging. In this state, the non-injection end shield 40 (also referred to herein as the "second shield") is extended, covering the needle cannula 20, and ready for assembly to a pen injector. The pen injector 190 (shown in FIG. 2), also sometimes referred to herein as the cartridge, comprises a vial of medication. The "pen injector" or "cartridge" may refer to the housing, or to the whole assembly including the vial, as the case may be. The pen injector 190 may be adapted for insertion into recess 54 of the hub 11 by a threaded connection, but the particular mechanism of inserting and retaining the pen injector in the hub is not critical.

In the non-patient end of the device, the second elastic member, interlock clip 60, presses into the needle mounting boss 30. The safety pen may comprise one or a plurality of such clips having flag 100, assembled to the boss with the clip component against the hub middle wall 50 separating the injection end recess 52 and the non-injection end recess 54 of the hub (also referred to herein as the "first recess" and the "second recess," respectively).

Second shield 40 is assembled to the inside of the hub via one or more alignment tabs 90 on the side of the shield. The alignment tabs have sufficient elasticity to snap into slots 92 positioned on the hub. This secures the shield to the hub and permits coaxial travel of the hub and shield. A compression spring 80 located between the inside of the shield 40 and supported on the interlock clip 60 positioned against the hub, provides the force required to maintain the shield at the full travel position, covering the needle cannula.

As used herein, the shield or shields "cover" the respective ends of the needle when the tip of the needle does not extend beyond the end wall of the respective shield, notwithstanding that the tip of the needle may be quite close to the aperture in the respective shields, and exposed to view.

A non-injection end spring 80 located between the second shield and the hub may be used to bias the shield to cover the non-injection end of the needle before the pen injector is installed. The spring 80 is compressed when the pen injector is installed. The spring 80 also maintains the position of the shield relative to the clips 60 to facilitate assembly and to prevent premature deployment of clip flags 100 into the engagement holes in the shield. In the unlocked position shown in FIG. 1, the engagement clips 60 are under tension caused by contact of the interlock clip making intimate contact against the inside wall of the shield 40, with clips 60 being held radially inward of the engagement holes in the shield. As a result of the tension applied by the clip tabs to the inside of the shield, the clip tabs spring into the receiving portions in the shield (which may be aided by ramp features leading to the openings, not shown) when the pen injector is removed. This mechanism functions as a dead stop, preventing the shield from further movement in relation to the non-injection end of the needle and hub and fixes the position of the shield to surround the non-injection end of the needle to prevent accidental needle sticks.

Another spring 180 on the injection end of the device between the first shield and the hub is compressed when pressure is applied on the first shield to administer an injection.

Figure 2:
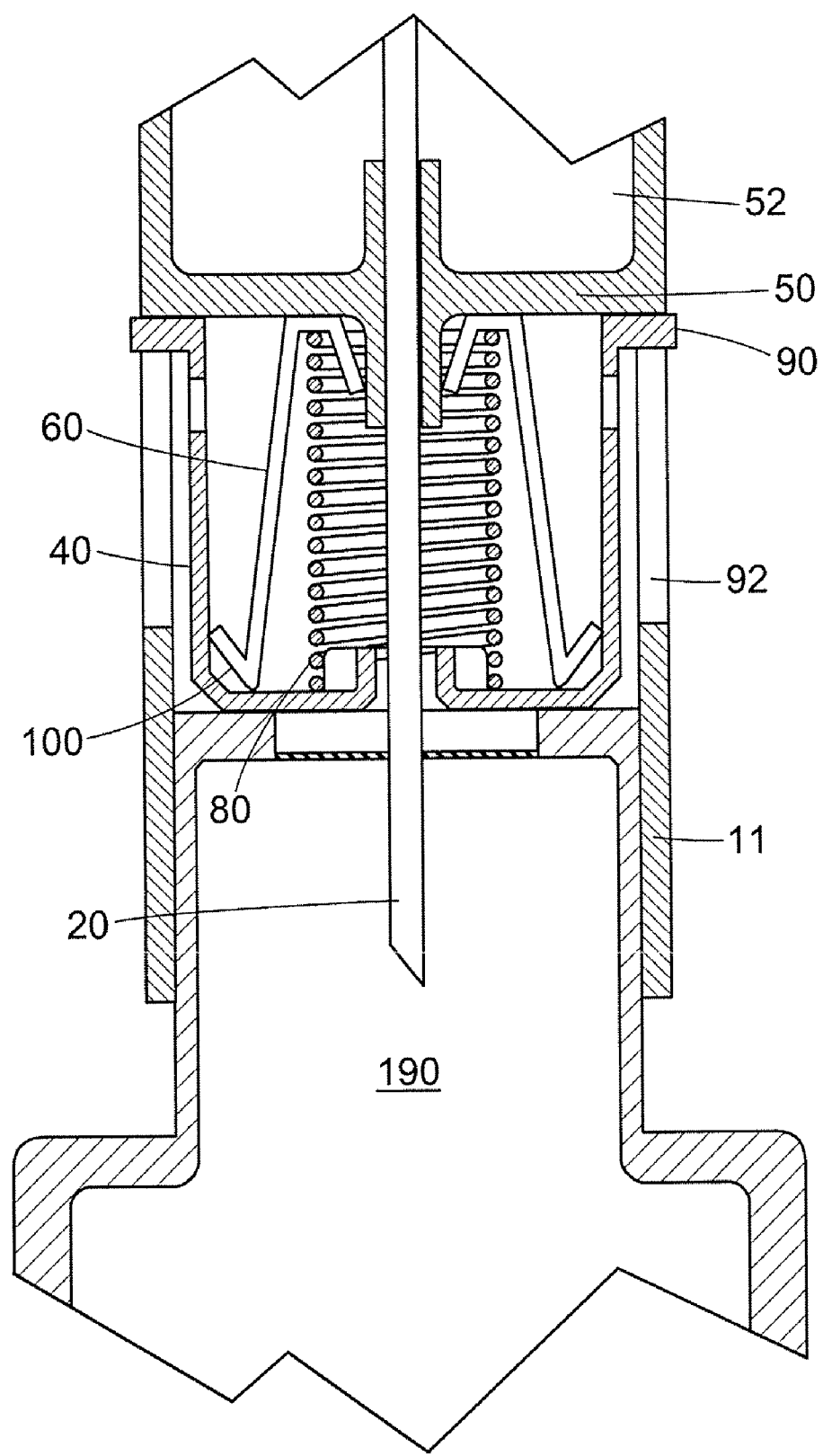
FIG. 2 is a detail of the system according to the invention showing the non-injection end shield in its compressed position with the pen injector installed.

FIG. 2 shows the non-injection end of a safety pen needle according to the invention after it has been assembled to the barrel of a pen injector device. This is the state of the invention found when the pen injector is being primed, dosed, and prior to and during injection. The shield 40 is sandwiched between the barrel of the pen injector and the hub middle wall 50. The resultant spatial relationship between the needle and the pen injector permits sufficient penetration depth so that the needle may access medicament from the pen cartridge. The alignment tab 90 of the shield is at the full travel position at the end of through-slots 92 that run axially along the hub 11.

Figure 3:
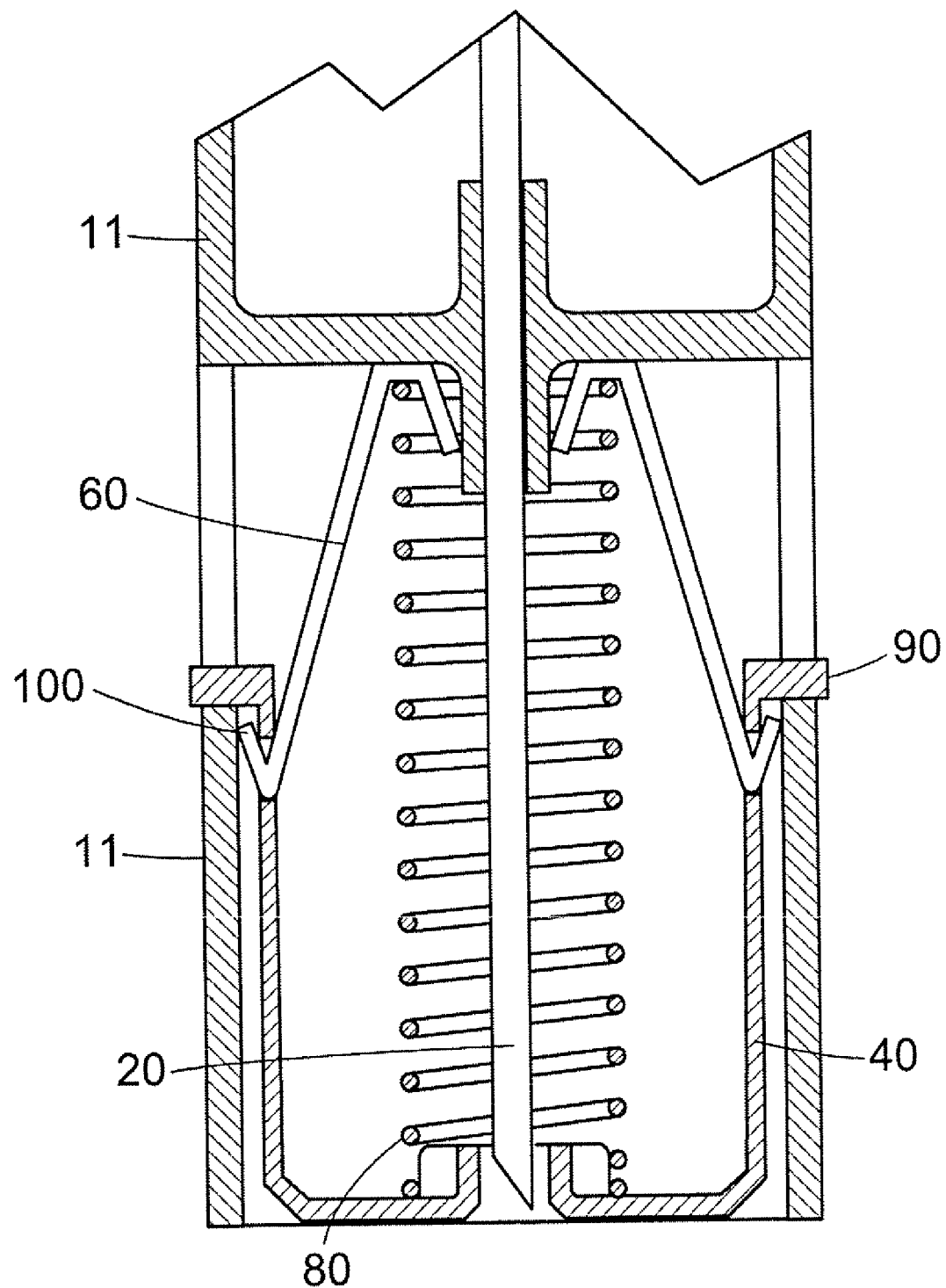
FIG. 3 is a detail of the system according to the invention showing the non-injection end shield after the pen injector has been removed, in the full travel position covering the needle cannula and locked in place by the clip.

In FIG. 3, the second elastic member is a clip 60 positioned against the middle wall 50 of the hub and the needle mounting 30. Flag 100, in a locked position, engages a slot in a radial wall of the second shield, preventing it from moving back up inside the hub.

Figure 4:
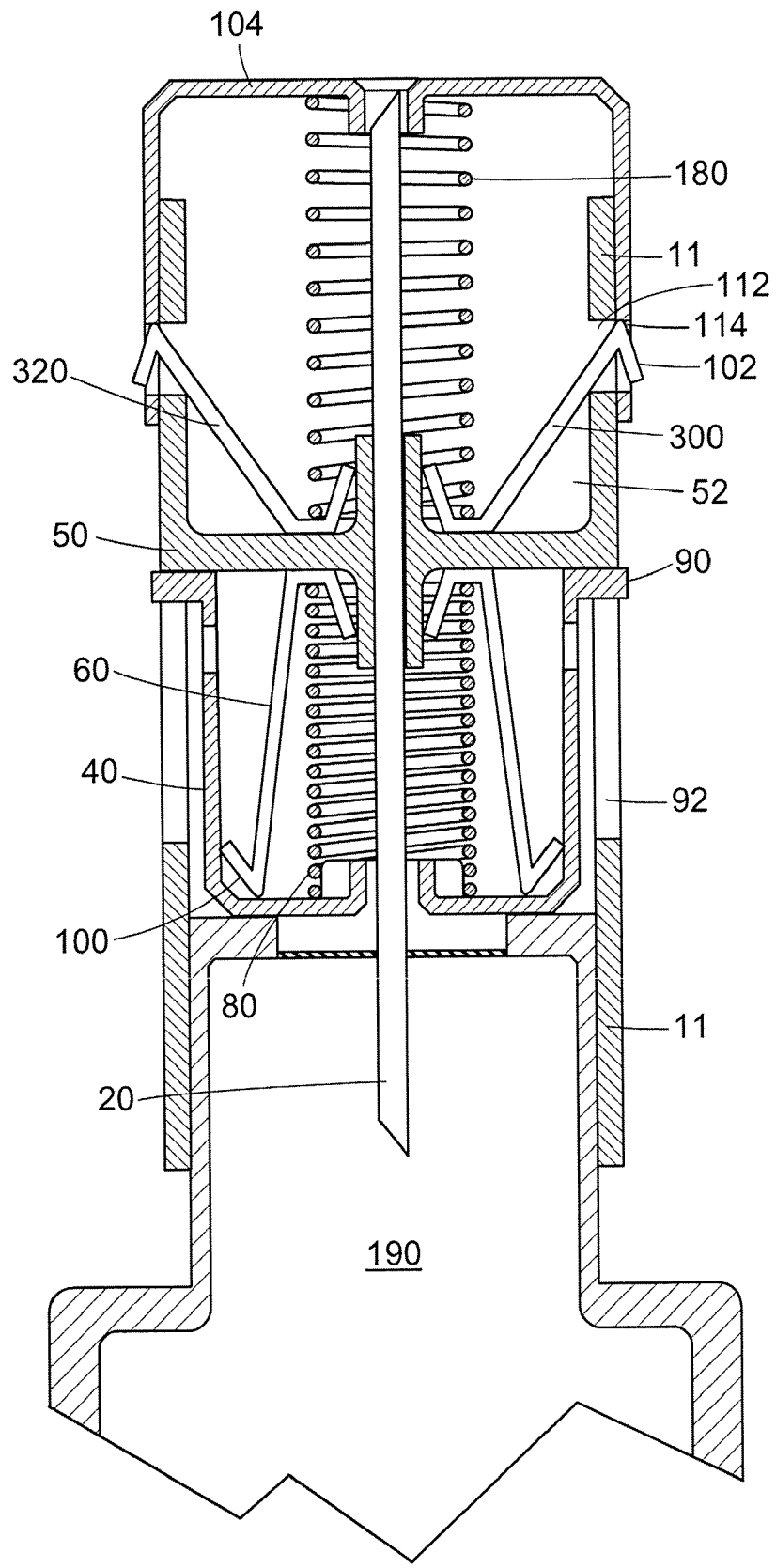
FIG. 4 schematically shows a device according to the invention with the pen injector installed on the non-injection end and the injection end shield in a locked position.

In FIG. 4, on the injection-end of the device, a plurality of first clips 300, 320 are shown positioned against the middle wall 50 of the hub 11. Each of the clips has a flag 102 that, in a locked position, engages hub slots 112 in the hub. and shield slots 114 the first shield 104, with the shield covering the needle 20.

Although the clips are shown in the Figures as separate parts on opposite sides of the hub middle wall, it is contemplated that the first and second elastic members, or clips, could be made as integral parts. In this context, "integral" simply means that the members could be connected. One or more clips are contemplated on either end of the device, with a plurality being preferred, as shown in the Figures.

The invention can be configured such that it can be applied to injection devices with dual needles, other than Type A pen injectors.

The foregoing description of the preferred embodiments is for illustration only and is not intended to limit the invention defined in the appended claims. For example, alternatives to a flexing sheet stainless steel interlock clip/tab component could be a molded, reinforced plastic or elastomeric clip/tab component. The passive safety mechanism could be embodied such that the clips with tabs are made integral to the shield and not attached to the hub while the hub incorporates blind holes for the tabs to engage. Alternatives to the compression spring include a helical spring, wave spring(s), Belleville, split washer, airpot type, elastomeric springs, flexing beams/fingers, molded-in springs etc.

What is claimed is:

1. A safety shield system for an injection pen needle comprising:
   a needle hub;
   a needle mounted in the hub and having an injection end and a non-injection end, wherein the hub has a first recess surrounding the injection end of the needle and a second recess surrounding the non-injection end of the needle to receive a pen-injector;
   a first shield moving coaxially over the first recess of the hub and having an aperture in an end wall thereof for passage of the needle, and traveling from a retracted position in which the needle is exposed to a full travel position in which the shield covers the injection end of the needle;
   a second shield moving within the second recess of the hub and having an aperture to permit passage of the non-injection end of the needle into the pen-injector, and traveling inside the second recess from a position in which the pen injector is installed in the hub to a full travel position in which the pen injector is removed from the hub and the second shield covers the non-injection end of the needle;
   a first elastic member housed between the first shield and the hub, engaging the first shield to hold the first shield in the full travel position;
   a second elastic member housed between the second shield and the hub, engaging the second shield to hold the second shield in its full travel position; and wherein
   the first elastic member is a clip positioned against the hub and having a tab that in a locked position engages aligned slots in both the radial wall of the hub and the radial wall of the first shield.

2. The safety shield system of claim 1, wherein
   the second elastic member is a clip positioned against the the hub and having a tab that in a locked position engages a slot in a radial wall of the second shield.

3. The safety shield system of claim 2, further comprising a non-injection end spring located between the second shield and the hub and supported on a clip positioned against the hub, the spring being compressed when the pen injector is installed.

4. The safety shield system of claim 1, further comprising an injection end spring between the first shield and the hub, the spring being compressed when pressure is applied on the first shield to administer an injection.

5. The safety shield system according to claim 1, wherein the tabs of the first elastic member are visible from the exterior of the pen needle when said tabs engage said slots in the radial wall of the shield.

6. The safety shield system according to claim 5, wherein the tabs of the first elastic member are provided with indicators visible from the exterior of the pen needle.

7. The safety shield system according to claim 1, wherein the first elastic member and the second elastic member constitute an integral part.

8. A safety shield system for an injection pen needle comprising:
   a needle hub;
   a needle mounted in the hub and having an injection end and a non-injection end, wherein the hub has a first recess surrounding the injection end of the needle and a second recess surrounding the non-injection end of the needle to receive a pen-injector;
   a first shield moving coaxially over the first recess of the hub and having an aperture in an end wall thereof for passage of the needle, and traveling from a retracted position in which the needle is exposed to a full travel position in which the shield covers the injection end of the needle;
   a second shield moving within the second recess of the hub and having an aperture to permit passage of the non-injection end of the needle into the pen-injector, and traveling inside the second recess from a position in which the pen injector is installed in the hub to a full travel position in which the pen injector is removed from the hub and the second shield covers the non-injection end of the needle;
   a first elastic member housed between the first shield and the hub, engaging the first shield to hold the first shield in the full travel position;
   a second elastic member housed between the second shield and the hub, engaging the second shield to hold the second shield in its full travel position, wherein
   the hub has a middle wall separating the first recess and the second recess and a needle mounting abutting the hub middle wall on opposite sides of the hub middle wall, the needle being mounted in the needle mounting; wherein
   the first elastic member is a clip positioned against the middle wall of the hub and the needle mounting having a tab that in a locked position engages slots in both the radial wall of the hub and the radial wall of the first shield; and wherein
   the second elastic member is a clip positioned against the middle wall of the hub and the needle mounting having a tab that in a locked position engages a slot in a radial wall of the second shield.

* * * * *